(12) United States Patent
Yin et al.

(10) Patent No.: US 11,499,897 B2
(45) Date of Patent: Nov. 15, 2022

(54) DEFORMATION CONTROLLABLE COMPRESSION RING-BASED MECHANICAL TEST SYSTEM FOR ROCKS WITH VARIABLE STIFFNESS AND TEST METHOD THEREOF

(71) Applicant: SHANDONG UNIVERSITY OF SCIENCE AND TECHNOLOGY, Qingdao (CN)

(72) Inventors: Yanchun Yin, Qingdao (CN); Tongbin Zhao, Qingdao (CN); Yunliang Tan, Qingdao (CN); Minglu Xing, Qingdao (CN); Yubao Zhang, Qingdao (CN); Kai Fang, Qingdao (CN); Chen Yan, Qingdao (CN)

(73) Assignee: SHANDONG UNIVERSITY OF SCIENCE AND TECHNOLOGY, Qingdao (CN)

( * ) Notice: Subject to any disclaimer, the term of this patent is extended or adjusted under 35 U.S.C. 154(b) by 0 days.

(21) Appl. No.: 17/715,752

(22) Filed: Apr. 7, 2022

(65) Prior Publication Data
US 2022/0283064 A1     Sep. 8, 2022

Related U.S. Application Data

(63) Continuation of application No. PCT/CN2021/082499, filed on Mar. 23, 2021.

(30) Foreign Application Priority Data

Mar. 6, 2021 (CN) .......................... 202110247634.7

(51) Int. Cl.
*G01N 3/10* (2006.01)
*G01N 33/24* (2006.01)
*G01N 3/06* (2006.01)

(52) U.S. Cl.
CPC .................. *G01N 3/10* (2013.01); *G01N 3/06* (2013.01); *G01N 33/24* (2013.01);
(Continued)

(58) Field of Classification Search
CPC ............ G01N 3/10; G01N 3/06; G01N 33/24; G01N 2203/0019; G01N 2203/0048; G01N 2203/06
See application file for complete search history.

(56) References Cited

U.S. PATENT DOCUMENTS

| 3,797,303 A | 3/1974 | Bascoul et al. |
| 5,323,655 A * | 6/1994 | Eagan .................... G01N 1/286 73/84 |
| 2019/0107472 A1 | 4/2019 | Alstrin |

FOREIGN PATENT DOCUMENTS

| CN | 103792133 A | 5/2014 |
| CN | 205719807 U | 11/2016 |

(Continued)

OTHER PUBLICATIONS

International Search Report of PCT/CN2021/082499, dated Nov. 25, 2021.

*Primary Examiner* — Jonathan M Dunlap

(57) ABSTRACT

The present invention discloses a deformation controllable compression ring-based mechanical test system for rocks with variable stiffness and a test method thereof, which comprises a loading device, a variable stiffness regulating device, a data monitoring system and a controlling system; the energy storing spring in the loading device allows the rebounding direction of the loading device to be contrary to the strain direction of the test-piece, which eliminates the energy supplement of the loading device to the test-piece and realizes the loading of an oversized stiffness on the test system; the variable stiffness regulating device precisely regulates the loaded stiffness by regulating the loaded stiff- (Continued)

ness of the test system according to test requirements, which realizes the test of loading different stiffness on the same test system and avoids the influences of differences to loading parameters between different test systems on the test results.

6 Claims, 4 Drawing Sheets

(52) U.S. Cl.
CPC ............... *G01N 2203/0019* (2013.01); *G01N 2203/0048* (2013.01); *G01N 2203/06* (2013.01)

(56) References Cited

FOREIGN PATENT DOCUMENTS

| | | | |
|---|---|---|---|
| CN | 109253932 | A | 1/2019 |
| CN | 109269902 | A | 1/2019 |
| CN | 110031320 | A | 7/2019 |
| CN | 110031321 | A | 7/2019 |
| CN | 110095345 | A | 8/2019 |
| CN | 209927633 | U | 1/2020 |

\* cited by examiner

DEFORMATION CONTROLLABLE COMPRESSION RING-BASED MECHANICAL TEST SYSTEM FOR ROCKS WITH VARIABLE STIFFNESS AND TEST METHOD THEREOF

CROSS-REFERENCE TO RELATED APPLICATIONS

This application is a continuation of International Patent Application No. PCT/CN2021/082499 with a filing date of Mar. 23, 2021, designating the United States, now pending, and further claims priority to Chinese Patent Application No. 202110247634.7 with a filing date of Mar. 6, 2021. The content of the aforementioned applications, including any intervening amendments thereto, are incorporated herein by reference.

TECHNICAL FIELD

The present invention belongs to the technical area of rock mechanical tests, more specifically a deformation controllable compression ring-based mechanical test system for rocks with variable stiffness and a test method based on the mechanical test system for rocks with variable stiffness.

BACKGROUND

The indoor rock mechanical test can simulate the material property and loading conditions of loading bodies in the engineering field through test systems of different types and different loading types. When destabilization failure occurs to loaded rocks, the top plate of different stiffness provides different energy complementary quantity to loaded rocks, which further causes differences to the destabilization failure form of loaded rocks. When studying the influence of the stiffness of the top plate on the mechanical property of rocks, requirements on top plates of different stiffness can be met by changing the loaded stiffness in the test system.

Specific to the traditional rock mechanical test system, a loaded stiffness in a single test system is always constant and can only be loaded under a specific large stiffness condition or a small stiffness condition, which fails to study the failure characteristic of rock test-pieces under different loaded stiffness conditions; however rock mechanical tests conducted on multiple test systems loaded with different stiffness can hardly ensure the consistency of parameters loaded and monitored between test systems. Therefore, in order to study the failure characteristic of rock test-pieces under different loaded stiffness conditions, it is necessary that the loaded stiffness in a single test system can be variable.

Patent literature 1 provides an inner and outer frame combined mechanical testing machine for rocks with variable stiffness and a test method thereof; patent literature 2 provides a mechanical test system for rocks with regulable loaded stiffness. The above two patent literatures all conducts tests of loading different stiffness in a single test system. This kind of the test system changes the loaded stiffness of the test system through regulating the stiffness of the test-piece within the upper frame part, but as the stiffness value of the test-piece within the cushion block part is always low and is not controllable, the stiffness value of the test system as a whole is comparatively low.

At the same time, the looseness of the frames connection sites cannot be avoided, which will further decrease the stiffness of the test system as a whole, allows a low upper limit to the stiffness of the test system loaded and small scope for the regulable loaded stiffness and fails to monitor and control of the structural deformation of the test system caused by looseness in the connection site, thereby influencing the accurate regulation of the test system on the actually loaded stiffness.

Therefore, there is a need to design a mechanical test system for rocks with variable stiffness where the loaded stiffness of the test system has a large regulation scope and can be accurately controlled so as to study influences of loaded stiffness in different test systems on the destabilization failure of the test-piece.

REFERENCES

Patent literature 1: publication number CN110031320A, disclosed on Jul. 19, 2019;

Patent literature 2: publication number CN109269902A, disclosed on Jan. 25, 2019.

SUMMARY OF THE INVENTION

One purpose of the present invention is to provide a deformation controllable compression ring-based mechanical test system for rocks with variable stiffness so as to regulate the loaded stiffness of the test system within a large stiffness scope based test requirements while accurately regulating the loaded stiffness.

The present invention adopts the following technical solutions in order to achieve the above purpose:

A deformation controllable compression ring-based mechanical test system for rocks with variable stiffness, comprising a loading device, a variable stiffness regulating device, a data monitoring system and a controlling system, wherein the loading device comprises an outer frame, a loading cylinder, a lift loading beam, an energy storing spring and a loading beam lifting and driving mechanism;

the cylinder block of the loading cylinder is mounted on the top of the outer frame and the loading cylinder faces towards the bottom;

the loading beam lifting and driving mechanism is connected to the lift loading beam and is used to drive the up-and-down motion of the lift loading beam;

the loading beam lifting and driving mechanism comprises a plurality of vertically provided ball screws and a screw driving motor;

wherein, the upper end of each ball screw is mounted on the top of the outer frame through a top screw supporting seat and the lower end of each ball screw is mounted on the base of the outer frame through a bottom screw supporting seat;

the nuts where the lift loading beam corresponds to each ball screw are respectively provided with one nut punch and the nuts in each of the ball screw respectively penetrate upwardly through the lift loading beam via one of the nut punches;

a ball bearing is provided respectively between the nut in each of the ball screw and the inner wall of the nut punch corresponding to the respective nut;

a plurality of the energy storing spring are respectively provided in the nuts of each ball screw; wherein, the upper end of the energy storing spring is connected to the bottom of the lift loading beam and the lower end of the energy storing spring is connected to the lower part of the nut;

the variable stiffness regulating device comprises a compression ring, a stiffness regulating cylinder, a buffer spring and a limit rope;

wherein, a top beam of the compression ring is connected to the bottom of the lift loading beam; the stiffness regulating cylinder is located inside of the compression ring, the cylinder block of the stiffness regulating cylinder is fixed on the top beam of the compression ring and the stiffness regulating cylinder faces towards the bottom;

the upper end of the buffer spring is connected to the cylinder block of the stiffness regulating cylinder and the lower end of the buffer spring is connected to a piston rod of the stiffness regulating cylinder;

a plurality of the limit ropes are provided and the top and the bottom of each limit rope are respectively connected correspondingly to the top beam and a bottom beam of the compression ring;

the data monitoring system comprises a first pressure transducer, a second pressure transducer, a third pressure transducer and a displacement sensor;

wherein, the first pressure transducer is provided between the loading cylinder and the lift loading beam;

the second pressure transducer is provided between the stiffness regulating cylinder and the bottom beam of the compression ring;

the third pressure transducer is provided on the base of the outer frame and a test-piece drop zone is provided the above of the third pressure transducer;

one end of the displacement sensor is connected to the top beam of the compression ring and the other end of the displacement sensor is connected to the bottom beam of the compression ring;

wherein, the loading cylinder, the screw driving motor, the stiffness regulating cylinder, the first pressure transducer, the second pressure transducer, the third pressure transducer and the displacement sensor are respectively connected to the controlling system through a cable.

Preferably, the compression ring is made of a spring; a side wall of the compression ring is an arc side wall.

Preferably, the limit rope is made of a stable rope or a stable cable.

The second purpose of the present invention is to provide a test method of loading oversized stiffness in a test system. This method is based on the above mechanical test system for rocks with variable stiffness according to meet test requirements of loading oversized stiffness.

The present invention adopts the following technical solutions in order to achieve the above purpose:

A test method of loading oversized stiffness in a test system including the following steps:

I.1. the controlling system controls the loading cylinder to load the lift loading beam;

I.2. after the lift loading beam is loaded, simultaneously loading the energy storing spring and the variable stiffness regulating device and further loading a test-piece placed above the base of the outer frame through the variable stiffness regulating device;

I.3. the loading on the test-piece is continued until the destabilization failure occurs, after the test-piece undergoes destabilization failure, the controlling system controls the loading cylinder to stop loading, the energy storing spring rebounds upwardly to drive the lift loading beam and enable the lift loading beam to closely abut the loading cylinder, thereby realizing the loading of the oversized stiffness.

The third purpose of the present invention is to provide a regulation method for the stiffness loaded in a test system. This method is based on the above mechanical test system for rocks with variable stiffness so as to achieve the regulation on the loaded stiffness in the test system.

The present invention adopts the following technical solutions in order to achieve the above purpose:

A regulation method for the stiffness loaded in a test system including the following steps:

II.1. before loading the test, the required stiffness value loaded in the test system is set in the controlling system, i.e. presetting the loaded stiffness value;

II.2. after starting the loading, the third pressure transducer and the displacement sensor respectively feedback to the controlling system on the corresponding measured quantity in real time, the controlling system calculates the stiffness value actually loaded in the test system in accordance with the pre-determined function relationship;

II.3. the controlling system compares the actually loaded stiffness value with the preset and loaded stiffness value, after judgment, if:

the actually loaded stiffness value is smaller than the preset and loaded stiffness value, then the controlling system controls to increase the loading force of the stiffness regulating cylinder, decrease the deformation amount of the compression ring of low stiffness and increase the stiffness of the variable stiffness regulating device under the control of the controlling system;

the actually loaded stiffness value is bigger than the preset and loaded stiffness value, then the controlling system controls to decrease the loading force of the stiffness regulating cylinder, increase the deformation amount of the compression ring of low stiffness, and decrease the stiffness of the variable stiffness regulating device under the control of the controlling system;

changing the actually loaded stiffness value of the test system, ensuring the actually loaded stiffness value of the test system to maintain constant and equivalent to the preset and loaded stiffness value in the whole process by means of regulating the stiffness of the variable stiffness regulating device.

Preferably, the pressure value measured by the third pressure transducer is defined as $F(t)$ and the deformation value measured by the displacement sensor is defined as $X(t)$;

then in step II.2, the function relationship between the actually loaded stiffness $K_a$ of the test system set in the controlling system and the pressure value $F(t)$ measured by the third pressure transducer and the deformation value $X(t)$ measured by the displacement sensor is $K_a = F(t)/X(t)$.

The fourth purpose of the present invention is to provide a mechanical test method of loading different stiffness on rocks. The method is based on the above mechanical test system for rocks with variable stiffness so as to meet test requirements of loading different stiffness.

The present invention adopts the following technical solutions in order to achieve the above purpose:

A mechanical test method of loading different stiffness on rocks including the following steps:

III.1. placing the rock test-piece in the test-piece drop zone, the controlling system controls the rotation of the screw driving motor, the ball screw moves the lift loading beam and the variable stiffness regulating device to a proper height position to allow the bottom beam of the compression ring to contact with the test-piece;

III.2. setting the preset and loaded stiffness of the test system; then the loading cylinder starts to load and allow the test-piece to be loaded, after loading the test-piece, the data monitoring system transmits data from each sensor in real time to the controlling system;

III.3. the controlling system regulates the actually loaded stiffness in real time according to the feedback data of the data monitoring system and the preset and loaded stiffness, thereby ensuring the actually loaded stiffness to meet the preset and loaded stiffness and maintain constant in the loading process;

III.4. the loading of the loading device is continued until destabilization failure occurs to the test-piece so as to complete experiments of loading the designed stiffness;

III.5. setting different preset and loaded stiffness and conducting multiple loading so as to complete the mechanical test of loading different stiffness on rocks.

The present invention possesses the following advantages:

(1) the present invention regulates the loaded stiffness of the test system through the variable stiffness regulating device, which can conduct tests of loading different stiffness on one identical test system and avoids influences of differences to parameters loaded in different test systems on test results;

(2) the energy storing spring in the present invention enables the rebounding direction of the loading device to be contrary with the strain direction of the test-piece and eliminates the energy supplement of loading device to the test-piece part during the loading process, which achieves the loading of oversized stiffness in the test system with a large upper limit of the loaded stiffness;

The compression ring in the variable stiffness regulating of the present invention is made of mental materials with high elasticity deformation and high strength, wherein the two side walls of the compression ring are an arc thin wall structure, which ensures a small enough lower limit of the loaded stiffness in the test system;

The present invention controls the regulation of the loaded stiffness of the test system between the upper and lower limits through the variable stiffness regulating device, which achieves the regulation control on the loaded stiffness of the test system within a large scope;

(3) the loading device part in the present invention is an oversized stiffness structure, the stiffness regulating device part is a stiffness variable structure and the loaded stiffness of the test system is regulated only by the variable stiffness regulating device rather than by combination of the both, which means influences of parts out of the variable stiffness regulating device on the stiffness regulation process can be avoided and ensures the accuracy of regulation on the loaded stiffness of the test system;

(4) The present invention allows the test-piece to be placed between the variable stiffness regulating device and the base of the outer frame by regulating the upper and lower position of the lift loading beam without a cushion block and eliminates influences of gaps between the cushion block on the loaded stiffness of the test system;

(5) the piston rod of the stiffness regulating cylinder in the present invention is provided with a buffer spring, for which reason the instantaneous rebound velocity at which the oil cylinder unloads is effectively decreased and the energy supplement to the compression ring from the rebounding of the unloaded oil cylinder is avoided.

wherein, 1—loading device; 2—variable stiffness regulating device; 3—data monitoring system, 4—controlling system; 5—test-piece; 101—loading cylinder, 102—outer frame; 103—ball screw; 104—lift loading beam; 105—ball bearing; 106—energy storing spring; 107—the nut of the ball screw; 108—top screw supporting seat; 109—bottom screw supporting seat; 110—nut punch; 111—supporting table; 201—stiffness regulating cylinder, 202—compression ring; 203—buffer spring; 204—limit rope; 301—first pressure transducer, 302—displacement sensor; 303—second pressure transducer, 304—third pressure transducer.

DETAILED DESCRIPTION OF PREFERRED EMBODIMENTS

The present invention is further described in detail in combination with figures and specific embodiments:

Embodiment 1

The present embodiment describes a deformation controllable compression ring-based mechanical test system for rocks with variable stiffness, which regulates the loaded stiffness of the test system within a large scope according to test requirements while contributing to the precise regulation on the loaded stiffness.

Figure 1:
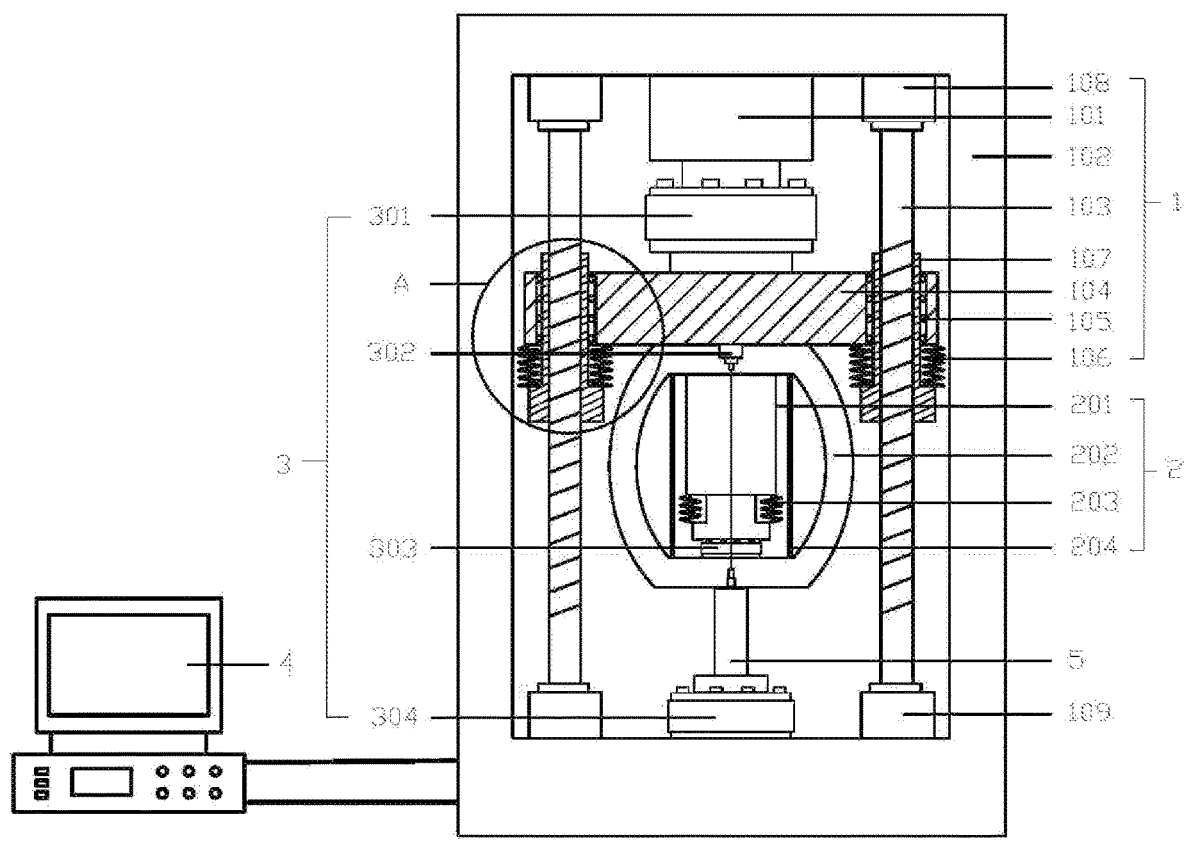
FIG. 1 is the structure diagram for the deformation controllable compression ring-based mechanical test system for rocks with variable stiffness of embodiments in the present invention.

As shown in FIG. 1, the deformation controllable compression ring-based mechanical test system for rocks with variable stiffness comprises a loading device 1, a variable stiffness regulating device 2, a data monitoring system 3 and a controlling system 4.

wherein, the loading device 1 in the present embodiment 1 is an oversized stiffness loading device, which comprises a loading cylinder 101, an outer frame 102, a lift loading beam 104, an energy storing spring 106 and a loading beam lifting and driving mechanism.

The loading cylinder 101 adopts a cylinder with high thrust. During the loading process, the loading cylinder 101 not only needs to load the lift loading beam 104 but also needs to overcome the elastic action of the energy storing spring 106 below.

The cylinder block of the loading cylinder 101 is mounted on the top (lower surface) of the outer frame 102 and faces towards the bottom.

Wherein, the loading cylinder 101 is connected to the controlling system 4 through a cable and the controlling system 4 controls the loading cylinder 101 to downwardly apply loads on the lift loading beam 104 and further loads the test-piece.

The outer frame 102 and the lift loading beam 104 are all made of materials with height elasticity modulus, such as bearing steel or ordinary steel.

The loading beam lifting and the driving mechanism are connected to the lift loading beam 104 and are used to drive the up-and-down motion of the lift loading beam 104.

The loading beam lifting and driving mechanism regulates the lift loading beam to move within a large scope, which can excellently fit the loading on test-pieces of different size, spares the need to add a cushion block between the test-piece and the test machine and avoids the influence of gaps in the cushion block on the loaded stiffness of the test system.

The loading beam lifting and driving mechanism in the present embodiment preferably adopts a screw driving mechanism.

As shown in FIG. 1, the loading beam lifting and driving mechanism comprises a ball screw 103, a top screw supporting seat 108, a bottom screw supporting seat 109 and a screw driving motor (Not shown in the figure).

Wherein, there are a plurality of ball screws 103, such as four, and each ball screw 103 respectively corresponds to one corner position of the lift loading beam 104 in the up and down direction. Take one of the ball screws 103 as an example:

The upper end of each ball screw 103 is mounted on the top of the outer frame 102 through a top screw supporting seat 108 and the lower end of each ball screw 103 is mounted in the bottom of the outer frame 102 through a bottom screw supporting seat 109.

After the mounting, all ball screws 103 are in a vertically placed state.

Wherein, the top screw supporting seat 108 and the bottom screw supporting seat 109 all adopt an existed screw supporting seat.

There is one screw driving motor, which can simultaneously drive the motion of each ball screw 103 through a screw driving motor. The screw driving motor can be provided in the outer frame 102 base.

The connection between the screw driving motor and the ball screw 103 is already known, which will not go into details.

The screw driving motor is connected to the controlling system 4. The controlling system 4 controls the rotation of the screw driving motor and drives the ball screw 103 to rotate. The screw driving motor in the present embodiment preferably adopts the server motor.

Figure 2:
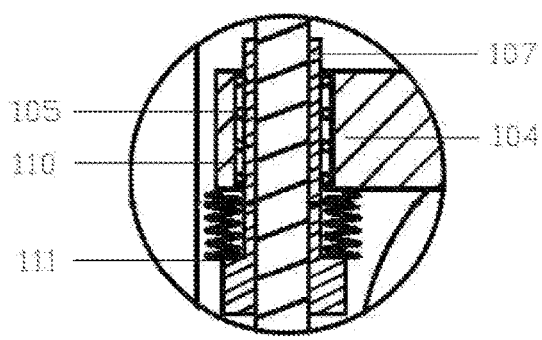
FIG. 2 is the enlarged view for part A in FIG. 1.

The nut 107 where the lift loading beam 104 corresponds to each ball screw is respectively provided with a nut punch 110. As shown in FIG. 2, the nut punch 110 is a through-hole that penetrates through the entire lift loading beam 104 up and down.

The nut 107 of each ball screw respectively penetrates through the lift loading beam 104 upwardly through a nut punch 110.

There are a plurality of energy storing springs 106, which respectively respond to the nut 107 provided in each ball screw.

Take one of the energy storing springs 106 as an example, the upper end of the energy storing spring 106 is connected to the lift loading beam 104 and the lower end of the energy storing spring 106 is connected to the lower part of nut 107 in the ball screw.

The energy storing spring 106 in the loading device 1 regulates the rebounding direction of the lift loading beam 104, which can eliminate the energy supplement from the rebounding of the loading device to the test-piece and further realize the loading of an oversized stiffness on the test system.

As shown in FIG. 2, the upper nut 107 in the ball screw has a cross section smaller than the lower thereof.

Where the upper nut 107 is connected to the lower of the nut 107 in the ball screw forms a supporting table 111, the lower end of the energy storing spring 106 is connected to the supporting table 111, which facilitates the support of the lift loading beam 104.

A ball bearing 105 is respectively provided between the nut 107 in each ball screw and the inner wall of nut punch 110 corresponding thereto, which weakens the friction between the nut 107 of the ball screw and the lift loading beam 104 through the ball bearing 105.

Figure 4A:
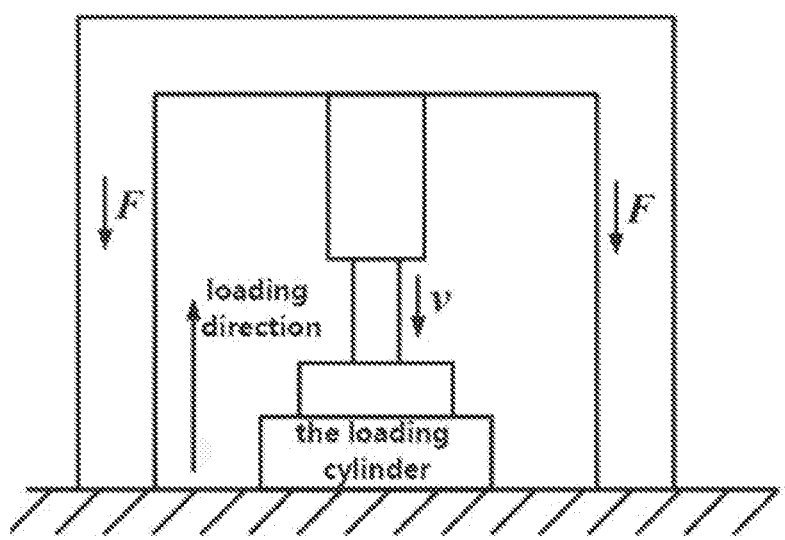
FIG. 4(a) and FIG. 4(b) are the schematic diagram for a regular loading and an oversized loading of embodiments in the present invention respectively.
Figure 4B:
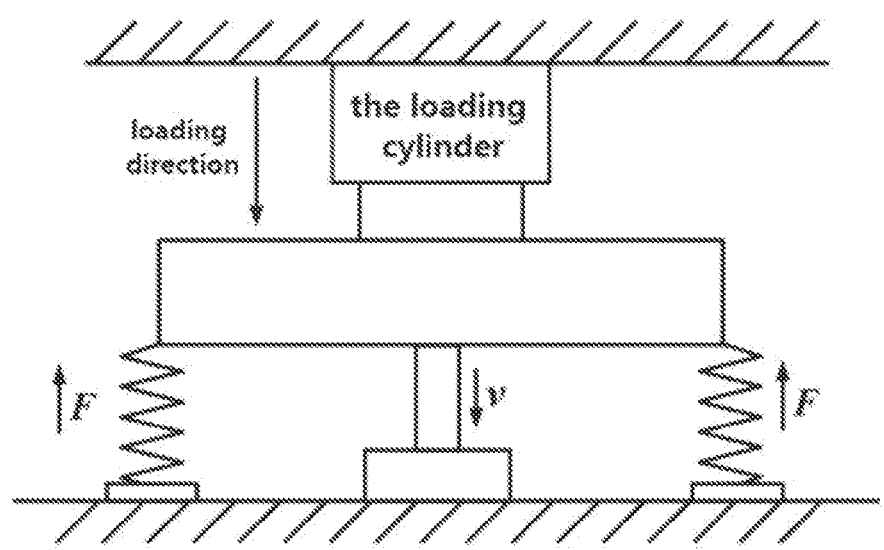

FIG. 4(a) and FIG. 4(b) respectively show the schematic diagram for the regular loading and the oversized stiffness loading in the present embodiment. It can know from the comparison between FIG. 4(a) and FIG. 4(b) that the principle of regulating the oversized stiffness in the present embodiment is:

By means of allowing the loading cylinder to load from top to bottom and providing an energy storing spring 106 below the lift loading beam 104, the direction of the counter-force provided to the loading beam by the frame is changed to a reverse direction of the strain direction of the test-piece, which allows the rebounding direction (in the present embodiment, it specifically means the rebounding direction of the lift loading beam 104) of the loading device to the strain direction of the test-piece, eliminates the energy supplement of the device loading an oversized stiffness to the test-piece part and realizes the loading of an oversized stiffness in the test system.

The variable stiffness regulating device 2 comprises a stiffness regulating cylinder 201, a compression ring 202, a buffer spring 203 and a limit rope 204.

Wherein, the compression ring 202 is a compression ring of low stiffness and this compression ring is made of spring steel.

Figure 3:
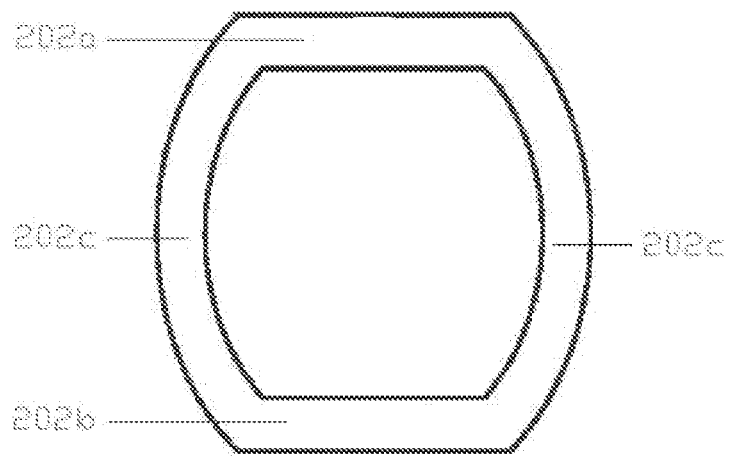
FIG. 3 is the structure diagram for the compression ring of embodiments in the present invention.

As shown in FIG. 3, two compression ring side walls 202c of the compression ring 202 preferably adopt an arc thin wall structure, for which reason a large compressive deformation can be produced in a vertical direction and the stiffness value thereof can be set as the minimum loaded stiffness value in the test system.

The compression ring top beam 202a is connected to the bottom of the lift loading beam 104, both of which are fixed together.

The stiffness regulating cylinder 201 is located in the inner side of the compression ring 202. The cylinder block of the stiffness regulating cylinder 201 is fixed on the compression ring top beam 202a and faces towards bottom. The stiffness regulating cylinder 201 is connected to the controlling system 4 through a cable.

The controlling system 4 controls the stiffness regulating cylinder 201 and regulates the deformation amount of the variable stiffness regulating device 2 to change the loaded stiffness.

There are a plurality of limit ropes 204, take one of the limit ropes 204 as an example:

The top of the limit rope 204 is fixed to the compression ring top beam 202a through a bolt and the bottom of the limit rope 204 is fixed to the compression ring bottom beam 202b through a bolt. Before the test, the limit rope 204 is regulated to a tension state.

The limit rope 204 functions to avoid an excessive rebounding of the compression ring 202 during loading, for which reason the limit rope 204 is preferably made of materials with strong toughness such as a stable rope or a stable cable, thereby making sure it withstands multiple impacting and loading.

The upper end of the buffer spring 203 is connected to the cylinder block of stiffness regulating cylinder 201 and the lower end of the stiffness regulating cylinder 201 is connected to the piston rod. The buffer spring 203 is used to weaken the rebounding action of the hydraulic oil when the test-piece is broken.

The spring before the test performs the loading is in a stretching state, which contributes to providing an upward stretching force for the piston rod of the stiffness regulating cylinder.

When the test-piece is broken, the existence of the stretching force can decrease the momentary rebounding speed when the stiffness regulating cylinder 201 is unloaded, which allows the rebounding speed thereof to be smaller than the rebounding speed of the bottom beam of the compression ring and avoids the energy supplement of the stiffness regulating cylinder to the compression ring 202.

The loaded stiffness of the test system is regulated by regulating the stiffness value of the variable stiffness regulating device 2 as a whole.

The stiffness regulating cylinder 201 changes the deformation of the compression ring 202, which can regulate the deformation amount of the variable stiffness regulating device 2, changes the energy storage capacity of the variable stiffness regulating device 2, regulates the stiffness thereof and further change the loaded stiffness of the test system.

The present embodiment allows the ball screw 103 to regulate the up and down location of the lift loading beam 104 and can ensure the test-piece to directly contact with the compression ring bottom beam 202b and the bottom of the outer frame 102, which means there is no need to place a cushion block between the test-piece and the latter two parts, thereby avoiding the influence of gaps between the cushion block and the cushion block and gaps between the cushion block and the test system on the stiffness value of the test system as a whole.

At the same time, the lift loading beam 104 can move up and down within a large scope, which can satisfy the loading of a test-piece of different sizes.

The data monitoring system 3 comprises a first pressure transducer 301, a displacement sensor 302, a second pressure transducer 303 and a third pressure transducer 304, wherein the disposition and function of each sensor are as follows:

The first pressure transducer 301 is provided between the loading cylinder 101 and the lift loading beam 104 and the first pressure transducer 301 is used to monitor the loading force of the loading cylinder 101.

The second pressure transducer 303 is provided between the stiffness regulating cylinder 201 and the compression ring bottom beam 202b and the second pressure transducer 303 is used to monitor the loading force of the stiffness regulating cylinder 201.

The third pressure transducer 304 is provided in the bottom of the outer frame 102 and above this third pressure transducer 304 is the drop zone of the test-piece 5. The third pressure transducer 304 is used to monitor the stress of the test-piece 5 and the variable stiffness regulating device 2 as a whole during the loading process, wherein the stress value of the test-piece 5 is substantially equal to the stress value of the variable stiffness regulating device 2 as a whole.

One end of the displacement sensor 302 is connected to the compression ring top beam 202a and the other end thereof is connected to the compression ring bottom beam 202b. The displacement sensor 302 is used to monitor the deformation of the compression ring 202 and this deformation value is equal to the deformation amount of the variable stiffness regulating device 2.

The first pressure transducer 301, the displacement sensor 302, the second pressure transducer 303 and the third pressure transducer 304 are respectively connected to the controlling system 4 through a cable and transmit monitoring data to the controlling system 4 in real time.

The controlling system 4 in the present embodiment can control the loading cylinder 101 to load the rock test-piece 5 until the destabilization failure occurs and performs regulation and control on the loaded stiffness in the test system through the stiffness regulating cylinder 201.

The principle regulating the loaded stiffness of the test system in the present embodiment is to change of the energy supplement value of the variable stiffness regulating device 2 to the test-piece 5 when the threshold of the test-piece is broken, thereby achieving the target of changing the loaded stiffness of the test system.

After the variable stiffness regulating device 2 is deformed by the counter force of the test-piece 5, the deformation energy is respectively stored in the stiffness regulating cylinder 201 and the compression ring 202. After the destabilization failure occurs to the test-piece, only the deformation of the compression ring 202 can downward supplement the test-piece 5;

When the compression ring 202 rebounds, the stiffness regulating cylinder 201 is detached from the compression ring 202 instantaneously under the action of the buffer spring 203 and the deformation of this part will not perform energy supplement to the test-piece 5;

Therefore, by means of changing the energy storage ratio between the stiffness regulating cylinder 201 and the compression ring 202, the deformation amount supplemented by the variable stiffness regulating device 2 to the test-piece 5 can be changed, thereby changing the loaded stiffness of the test system.

More specifically, the stiffness regulating cylinder 201 controls the deformation amount $X(t)$ of the compression ring 202 to regulate the energy storage ratio of the compression ring 202, thereby regulating the actually loaded stiffness $Ka$ of the test system.

When the compression ring 202 is not under the action of the stiffness regulating cylinder 201, the variable stiffness regulating device 2 can produce the maximum deformation amount $Xmax$ and the maximum deformation energy storage amount at the same time, wherein the loaded stiffness is the minimum loaded stiffness $Kmin$ of the test system at this time;

After stiffness regulating cylinder 201 loads the compression ring 202, the deformation amount of the compression ring 202 under the same stress of the test-piece gradually decreases and the ratio that the deformation energy storage amount of compression ring 202 accounts in the total energy storage of the variable stiffness regulating device also gradually decreases, thereby allowing the actually loaded stiffness $Ka$ of the test system to gradually increase; when the deformation amount of the compression ring 202 is kept as zero, the inside deformation energy storage ratio is zero, at which time the actually loaded stiffness in the test system reaches the maximum value $Kmax$ and can perform the loading of an oversized stiffness in combination with the method of loading an oversized stiffness by the above loading device.

Before loading, the controlling system 4 sets the preset and loaded stiffness value $Kp$ of the test system as any value between the $Kmin$ and the $Kmax$. After the loading, the controlling system 4 controls the stiffness regulating cylinder 201 and regulates the deformation amount of the compression ring 202, which can complete the loading test under a designed loaded stiffness of the test system by regulating the actually loaded stiffness of the test system to the preset and loaded stiffness value. The loading of different stiffness in one identical test system can be realized by setting different preset and loaded stiffness.

Embodiment 2

The present embodiment 2 describes a test method of loading oversized stiffness in a test system and this method is based on the mechanical test system for rocks with variable stiffness in embodiment 1 to meet requirement for tests of loading an oversized stiffness.

A test method of loading oversized stiffness in a test system, including the following steps:

I.1. the controlling system 4 controls the loading cylinder 101 to load the lift loading beam 104.

I.2. After the lift loading beam 104 is loaded, the energy storing spring 106 and the variable stiffness regulating device 2 are loaded, further loading the test-piece 5 placed above the base of the outer frame through the variable stiffness regulating device 2;

during the loading process, the rebounding direction of the lift loading beam 104 is contrary to the strain direction of the test-piece.

I.3. the test-piece 5 is continued to be loaded until the destabilization failure occurs. After the destabilization failure occurs to the test-piece, the controlling system 4 controls the loading cylinder 101 to stop loading, the energy storing spring 106 rebounds upward, drives the lift loading beam 104, allows it to abut upward the loading cylinder 101, which ensures that the loading device 1 does not supplement energy to the variable stiffness regulating device 2 and the test-piece 5 and realizes the loading of an oversized stiffness.

Embodiment 3

The present embodiment 3 describes a regulation method for the stiffness loaded in a test system and this method is based on the mechanical test system for rocks with variable stiffness in embodiment 1 to realize the regulation on the loaded stiffness of the test system.

Figure 5:
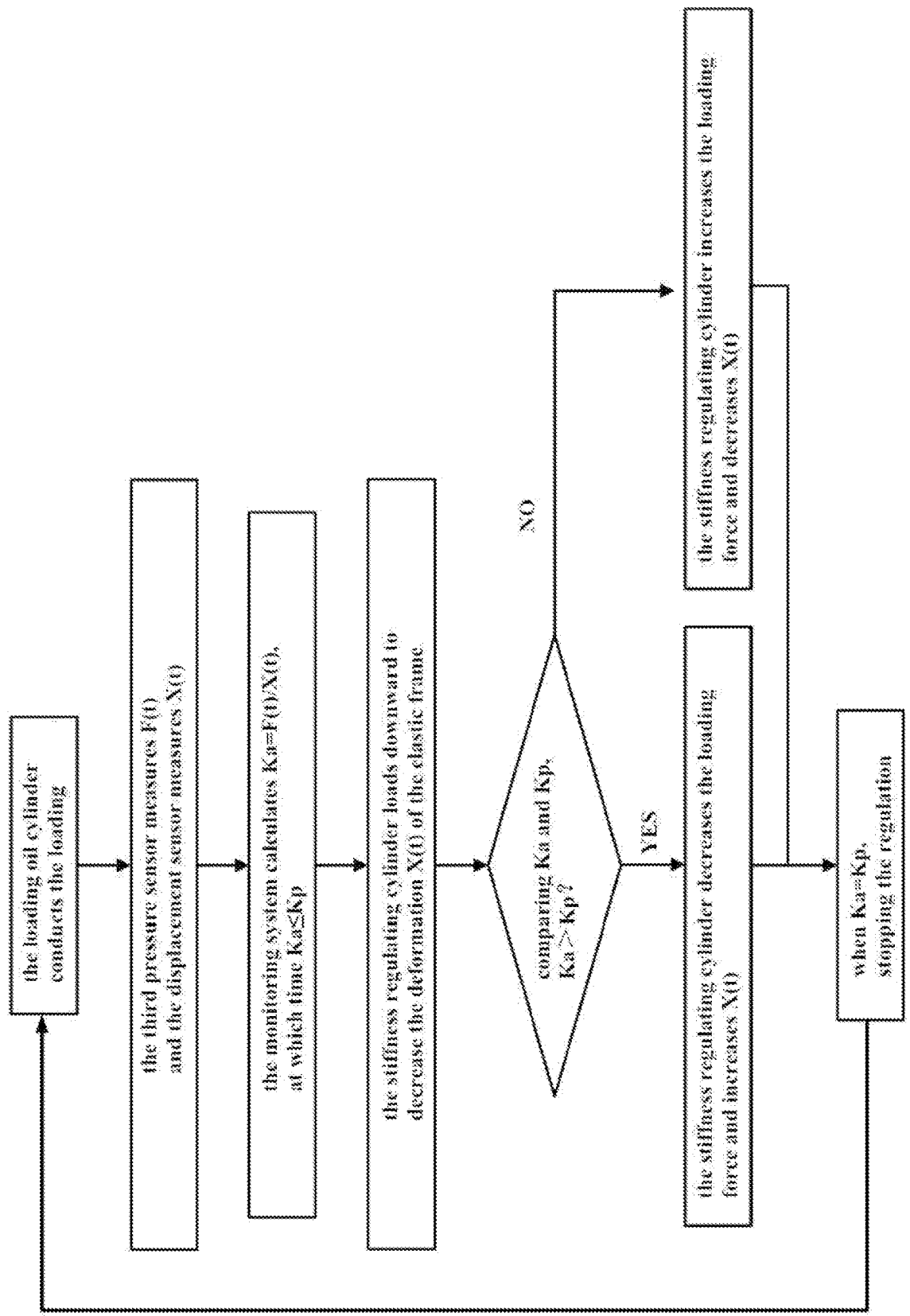
FIG. 5 is the process diagram for the regulation method for the stiffness loaded in a test system of embodiments in the present invention.

As shown in FIG. 5, the regulation method for the stiffness loaded in a test system includes the following steps:

II.1. before the test performs the loading, the required loaded stiffness, i.e. the preset and loaded stiffness Kp, of the test system is set in the controlling system.

II.2. after the loading starts, the third pressure transducer 304 and the displacement sensor 302 respectively feedback to the controlling system 4 in real time on the corresponding measured quantity and the controlling system calculates the actually loaded stiffness value Ka of the test system based on the predetermined function relationship.

The pressure value measured by the third pressure transducer as F(t) and the deformation value measured by the displacement sensor as X(t).

Then the function relationship between the actually loaded stiffness value Ka of the test system set in the controlling system 4 and the pressure value F(t) measured by the third pressure transducer and the deformation value X(t) measured by the displacement sensor is Ka=F(t)/X(t).

After the loading starts, the controlling system calculates the actually loaded stiffness value Ka of the test system based on the predetermined function relationship.

II.3. the controlling system compares the actually loaded stiffness value Ka with the preset and loaded stiffness value Kp, after confirmation, if:

the actually loaded stiffness value Ka is smaller than the preset and loaded stiffness value Kp, the controlling system 4 controls to increase the loading force of the stiffness regulating cylinder, decrease the deformation amount X(t) of the stiffness compression ring, increase the stiffness of the variable stiffness regulating device 2;

herein, the stiffness of the variable stiffness regulating device 2 is the actually loaded stiffness;

the actually loaded stiffness value Ka is bigger than the preset and loaded stiffness value Kp, the controlling system 4 controls to decrease the loading force of the stiffness regulating cylinder, increase the deformation amount X(t) of the stiffness compression ring, decrease the stiffness of the variable stiffness regulating device 2.

During the entire loading process, the data monitoring system 3 continues to monitor the stress F(t) and the deformation amount X(t) of the compression ring 202 and feedback to the controlling system 4 in real time. The controlling system 4 continues the repeat the present step, regulates the stiffness of the variable stiffness regulating device 2, changes the actually loaded stiffness value of the test system and ensures the actually loaded stiffness value of the test system to be constant and equal to the preset and loaded stiffness value in the whole process.

The data monitoring system 3 and the controlling system 4 in the present embodiment are in mutual coordination, which can control the variable stiffness regulating device 2 and further performs real time monitoring and precise regulation and control on the the loaded stiffness of the test system.

Embodiment 4

The present embodiment 4 describes a mechanical test method of loading different stiffness on rocks and this method is based on the mechanical test system for rocks with variable stiffness in embodiment 1 to meet different requirements for tests of loading the stiffness.

The mechanical test method of loading different stiffness on rocks includes the following steps:

III.1. the rock test-piece 5 is placed in the test-piece drop zone, the controlling system controls the screw driving motor to rotate, the ball screw 103 moves the lift loading beam 104 and the variable stiffness regulating device 2 to a proper height position, which allows the bottom beam of the compression ring to contact with the test-piece.

III.2. a preset and loaded stiffness is set for the test system; then, the loading cylinder 101 starts to load and further loads the test-piece 5. After loading the test-piece 5, the data monitoring system 3 transmits data of each sensor to the controlling system 4.

III.3. the controlling system 4 regulates the actually loaded stiffness in real time based on the feedback data from the data monitoring system 3 and the preset loaded stiffness, whose regulation process is the same with the regulation process of the loaded stiffness in embodiment 3;

the regulation on the loaded stiffness can ensure the actually loaded stiffness to meet the preset and loaded stiffness and maintain constant during the loading process.

III.4. the loading device 1 is continued to be loaded until the destabilization failure occurs to the test-piece 5 to complete tests of loading the designed stiffness;

III.5. setting different preset and loaded stiffness and performing multiple loading to complete mechanical tests for rocks loaded with different stiffness.

The data monitoring system 3 and the controlling system 4 are in coordination with the loading device 1 and the variable stiffness regulating device 2 in the present embodiment, which can regulates the loading force on the oil cylinder based on the monitored data in real time and control the test system to load the test-piece and regulate the actually loaded stiffness.

What is claimed is:

1. A deformation controllable compression ring-based mechanical test system for rocks with variable stiffness, comprising a loading device, a variable stiffness regulating device, a data monitoring system and a controlling system, wherein the loading device comprises an outer frame, a loading cylinder, a lift loading beam, an energy storing spring and a loading beam lifting and driving mechanism;

a cylinder block of the loading cylinder is mounted on a top of the outer frame and the loading cylinder faces downward;

the loading beam lifting and driving mechanism is connected to the lift loading beam and is used to drive an up-and-down motion of the lift loading beam;

the loading beam lifting and driving mechanism comprises a plurality of vertically provided ball screws and a screw driving motor;

wherein, an upper end of each ball screw is mounted on the top of the outer frame through a top screw supporting seat and a lower end of each ball screw is mounted on a base of the outer frame through a bottom screw supporting seat;

nuts where the lift loading beam corresponds to each ball screw are respectively provided with one nut punch and the nuts in each ball screw respectively penetrate upwardly through the lift loading beam via one of the nut punches;

a ball bearing is provided respectively between the nut in each ball screw and an inner wall of the nut punch corresponding to the nut in each ball screw;

the nuts of each ball screw are respectively provided with the energy storing spring; wherein, an upper end of the energy storing spring is connected to a bottom of the lift loading beam and a lower end of the energy storing spring is connected to a lower part of the nut;

the variable stiffness regulating device comprises a compression ring, a stiffness regulating cylinder, a buffer spring and a limit rope;

wherein, a top beam of the compression ring is connected to the bottom of the lift loading beam; the stiffness regulating cylinder is located inside of the compression ring, the cylinder block of the stiffness regulating cylinder is fixed on the top beam of the compression ring and the stiffness regulating cylinder faces downward;

an upper end of the buffer spring is connected to the cylinder block of the stiffness regulating cylinder and a lower end of the buffer spring is connected to a piston rod of the stiffness regulating cylinder;

a plurality of the limit ropes are provided and a top and a bottom of each limit rope are respectively connected correspondingly to the top beam and a bottom beam of the compression ring;

the data monitoring system comprises a first pressure transducer, a second pressure transducer, a third pressure transducer and a displacement sensor;

wherein, the first pressure transducer is provided between the loading cylinder and the lift loading beam;

the second pressure transducer is provided between the stiffness regulating cylinder and the bottom beam of the compression ring;

the third pressure transducer is provided on the base of the outer frame and a test-piece drop zone is provided above the third pressure transducer;

one end of the displacement sensor is connected to the top beam of the compression ring and the other end of the displacement sensor is connected to the bottom beam of the compression ring;

wherein, the loading cylinder, the screw driving motor, the stiffness regulating cylinder, the first pressure transducer, the second pressure transducer, the third pressure transducer and the displacement sensor are respectively connected to the controlling system through a cable.

2. The deformation controllable compression ring-based mechanical test system for rocks with variable stiffness according to claim 1, wherein the compression ring is made of a spring; a side wall of the compression ring is an arc side wall.

3. The deformation controllable compression ring-based mechanical test system for rocks with variable stiffness according to claim 1, wherein the limit rope is made of a stable rope or a stable cable.

4. A regulation method for the stiffness loaded in a test system and based on the deformation controllable compression ring-based mechanical test system for rocks with variable stiffness according to claim 1, wherein the regulation method includes the following steps:

II.1. before loading a test, a required stiffness value loaded in the test system is set in the controlling system to define as a preset loaded stiffness value;

II.2. after starting the loading, the third pressure transducer and the displacement sensor respectively feedback to the controlling system on the corresponding measured quantity in real time, the controlling system calculates an actually loaded stiffness value loaded in the test system in accordance with a pre-determined function relationship;

II.3. the controlling system compares the actually loaded stiffness value with the preset loaded stiffness value, after judgment, if:

the actually loaded stiffness value is smaller than the preset loaded stiffness value, then the controlling system controls to increase a loading force of the stiffness regulating cylinder, decrease a deformation amount of the compression ring of low stiffness and increase a stiffness of the variable stiffness regulating device;

the actually loaded stiffness value is bigger than the preset loaded stiffness value, then the controlling system controls to decrease the loading force of the stiffness regulating cylinder, increase the deformation amount of the compression ring of low stiffness, and decrease the stiffness of the variable stiffness regulating device;

changing the actually loaded stiffness value of the test system, ensuring the actually loaded stiffness value of the test system to maintain constant and equivalent to the preset loaded stiffness value in the whole process by means of regulating the stiffness of the variable stiffness regulating device.

5. The regulation method for the stiffness loaded in a test system according to claim 4, wherein a pressure value measured by the third pressure transducer is defined as $F(t)$ and a deformation value measured by the displacement sensor is defined as $X(t)$;

then in step II.2, the pre-determined function relationship between the actually loaded stiffness $Ka$ of the test system set in the controlling system and the pressure value $F(t)$ measured by the third pressure transducer and the deformation value $X(t)$ measured by the displacement sensor is $Ka=F(t)/X(t)$.

6. A mechanical test method of loading different stiffness on rocks and based on the deformation controllable compression ring-based mechanical test system for rocks with variable stiffness according to claim 1, wherein the test method includes the following steps:

III.1. placing a rock test-piece in a test-piece drop zone, the controlling system controls a rotation of the screw driving motor, the ball screw moves the lift loading beam and the variable stiffness regulating device to a proper height position to allow the bottom beam of the compression ring to contact with the rock test-piece;

III.2. setting the preset loaded stiffness value of the test system; then the loading cylinder starts to load and allow the rock test-piece to be loaded, after loading the rock test-piece, the data monitoring system transmits data from each sensor in real time to the controlling system;

III.3. the controlling system regulates the actually loaded stiffness value in real time according to the feedback data of the data monitoring system and the preset loaded stiffness value, thereby ensuring the actually loaded stiffness value to meet the preset loaded stiffness value and maintain constant in the loading process;

III.4. the loading of the loading device is continued until destabilization failure occurs to the rock test-piece so as to complete experiments of loading the designed stiffness;

III.5. setting a different preset loaded stiffness value and conducting multiple loading so as to complete the mechanical test of loading different stiffness on rocks.

* * * * *